United States Patent [19]
Landgren et al.

[11] Patent Number: 5,487,307
[45] Date of Patent: Jan. 30, 1996

[54] METHOD AND APPARATUS FOR TESTING CONCRETE EXPANSION

[75] Inventors: Robert Landgren, Cody, Wyo.; William F. Perenchio, Northfield, Ill.

[73] Assignee: Kalman Floor Company, Inc., Evergreen, Colo.

[21] Appl. No.: 194,452

[22] Filed: Feb. 10, 1994

[51] Int. Cl.⁶ .................................................. G01N 33/38
[52] U.S. Cl. .................... 73/803; 73/149; 73/866
[58] Field of Search .......................... 73/149, 803, 866; 338/2, 3, 6

[56] References Cited

U.S. PATENT DOCUMENTS 3,665,756  5/1972  Russell ........................................ 338/3
3,779,085 12/1973  Rice ........................................... 73/803
4,408,489 10/1983  Spangle ....................................... 73/866
4,943,930  7/1990  Radjy ......................................... 73/803

*Primary Examiner*—Thomas P. Noland
*Assistant Examiner*—Eric S. McCall
*Attorney, Agent, or Firm*—Watson, Cole, Grindle & Watson

[57] ABSTRACT

A method and apparatus is disclosed for measuring on-site expansive volumetric changes in hardened, shrinkage-compensated concrete samples. The sample is disposed in a cylindrical container having a strain gauge for measuring hoop stress which is correlated with expansion of the sample.

17 Claims, 4 Drawing Sheets

PAIL vs. ASTM 878 BAR EXPANSIONS AT LENGTH EQUILIBRIUM OR AFTER 4 DAYS OF EXPANSION

METHOD AND APPARATUS FOR TESTING CONCRETE EXPANSION

BACKGROUND OF THE INVENTION

The invention relates to a method and apparatus for determining expansive volumetric changes in curable materials. In particular, the invention relates to a method and apparatus for accurate on-site determination of expansive volumetric changes in relatively large aggregate size, hardened, shrinkage-compensated concrete. An example of shrinkage-compensated concrete is defined by America Concrete Institute Committee ACI 223. The test is operative without delay from the time of a concrete pour and employs a cylindrical container and a strain gauge for measuring hoop stress.

Portland cement used in concrete mixes results in a material that has about 0.04%–0.08% shrinkage over its lifetime. This results in surface cracking over time. Shrinkage-compensated concrete is a high performance material which, by means of expansive additives, compensates for normal shrinkage. This material is useful in applications where a high quality, crack free surface is required. In order to assure that the shrinkage-compensated concrete has a desired expansion characteristic, a test is needed to measure such expansion.

A currently available test for determining expansion of shrinkage-compensated concrete is set forth in ASTM designation C878. The test employs an elongated mold for casting a test specimen and a restraining cage consisting of a threaded steel rod and spaced-apart end plates secured to the rod. The restraining cage is placed in the mold and the material to be tested is compacted into the mold between the plates. After the material initially sets up or cures (six hours minimum), it is demolded and length measurements of the rod are taken at specific times over a period of seven days. At present, expansions in a range of 0.03 and 0.07 percent are considered to be suitable for reduction in ultimate shrinkage cracking in shrinkage-compensated concrete.

Although the C878 expansion test is the currently acceptable standard, it is difficult and costly to implement. For example, the test requires a skilled laboratory technician to perform it properly. The test procedure requires that the specimen is demolded not less than six hours after casting. In a field construction context, this means that the laboratory technician is operating on an overtime basis, or two shifts are required. Further, demolding fresh, weak, elongated concrete bars is a process requiring great delicacy and skill. It is not unusual for the molded sample to break during the demolding process. Also, there is a considerable delay between the time that the sample is cast and the first significant expansion measurement is taken, for example, an initial expansion measurement can only be taken after the sample is demolded. Consequently, bar expansions that occur after the concrete sets but before the first significant measurement may be made are not detected by the procedure.

The C878 test also places some limitation on the maximum size of coarse aggregate which may be employed in the samples. The mold in the ASTM test is 3"×3"×10" and the rod in the restraining cage is disposed centrally of the mold, limiting the size of the opening available for concrete entry and placement. This makes it difficult to fabricate samples with concrete containing large aggregate. In fact, the ASTM standard has a caution regarding the use of concrete containing coarse aggregate with a maximum size greater than about one inch.

Finally, measurement of length changes in the ASTM C878 test sample is time consuming and must be done in a laboratory by a skilled technician. Thus, there is a considerable expense involved.

It is therefore desirable to have available a method and apparatus for performing an on-site concrete expansion test. It is also desirable to have such a method and apparatus which requires less skill and time to perform as the currently available method. Further, it is desirable to have a method and apparatus for testing curable mixtures which provide instantly available information and which is not limited to the aggregate sizes as is the C878 test.

SUMMARY OF THE INVENTION

The present invention is based upon the discovery that measurements of expansive volumetric changes in hardenable curable concrete samples may be performed by utilization of an apparatus which comprises a container having an open top and a cylindrical sidewall for receiving the curable sample therein. A strain gauge is secured to the sidewall of the container and is disposed to sense circumferential expansion with the container as the volume of the sample changes. When energized by an electrical source, the strain gauge produces an output which may be correlated with the corresponding expansion and contraction of the sample.

In a method for measuring volumetric changes in hardened concrete samples, the apparatus above described is utilized for sensing such volumetric changes shortly after casting without demolding the sample.

DESCRIPTION OF THE INVENTION

Figure 1:
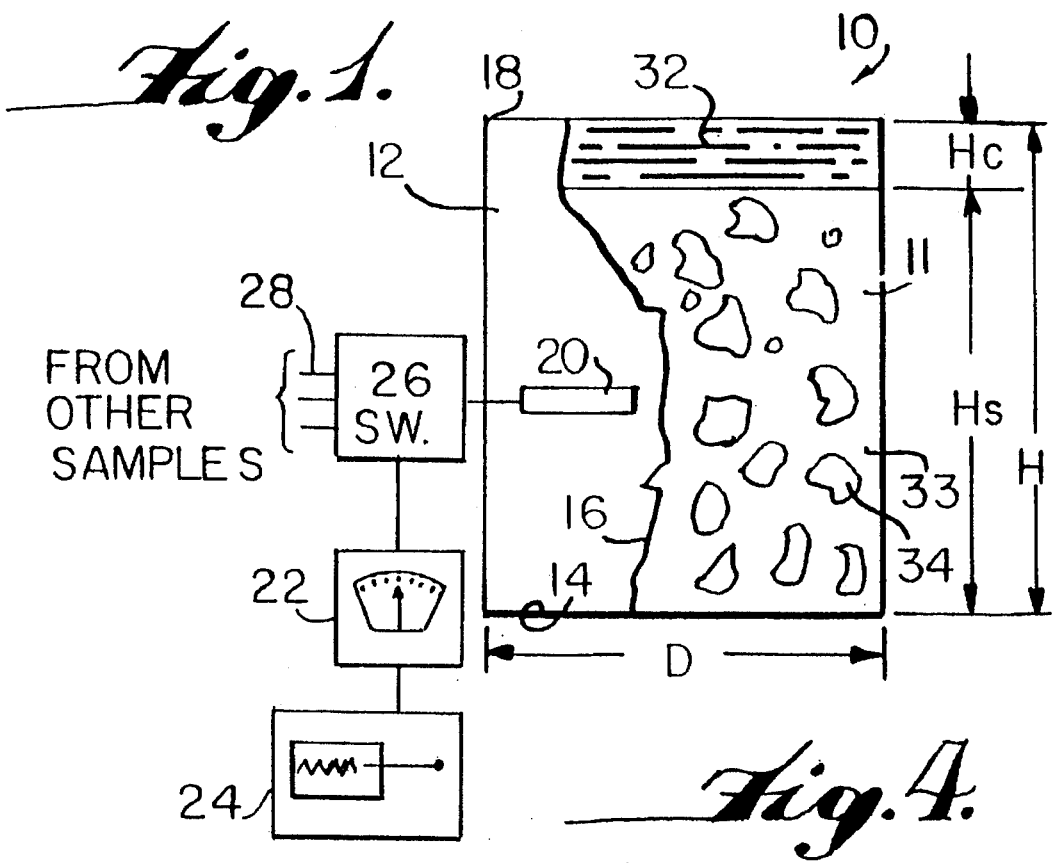
FIG. 1 is a fragmentary schematic illustration of a testing apparatus for measuring volumetric changes in a curable concrete sample.

FIG. 1 illustrates an apparatus 10 for testing expansive volumetric changes, of a hardenable sample 11, such as shrinkage compensated concrete. The apparatus 10 comprises a container 12 in the form of a right regular cylinder having a closed bottom 14, standing sidewall 16 and an open top 18. The cylinder 12 has at least one strain gauge 20 attached to the exterior of the upstanding sidewall 16 by a suitable adhesive, as illustrated. The strain gauge is electrically connected to a meter or detector 22. Changes in the length of the strain gauge 20 cause a corresponding change in the meter output.

Measurements are made by coupling the strain gauge 20 directly to the detector 22. If desired, measurements may be taken manually and periodically recorded. Alternatively, a digital data logging or pen recording device 24 may be coupled to the output of the detector 22. Additionally, a switch 26 having one or more inputs 28, may be coupled between the gauge 20 and the detector 22. If desired, multiple readings from other samples may be selectively taken by coupling the outputs of a plurality of containers 12 to corresponding ones of the multiple inputs 28 of the switch 26. The switch 26 may then be used to electronically or manually scan the inputs 28.

Figure 2A:
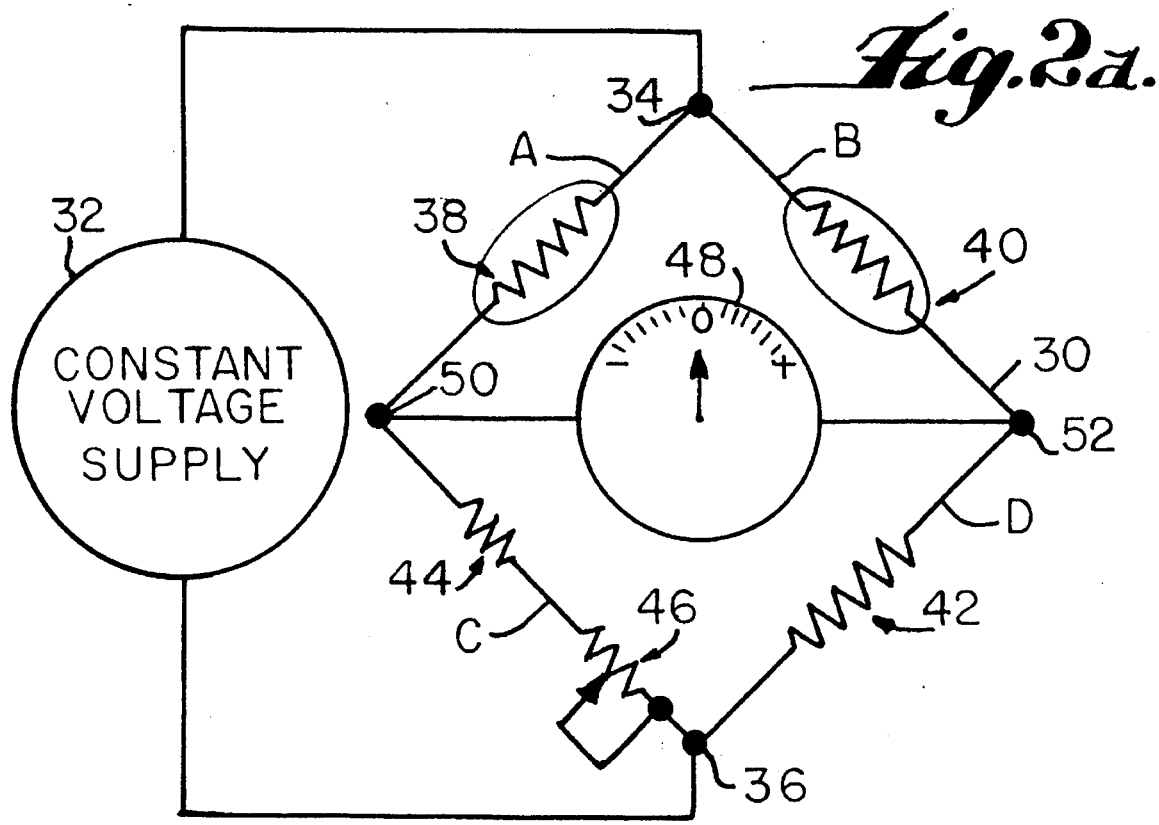
FIGS. 2A and 2B are schematic diagrams of exemplary strain gauge circuits which may be utilized in accordance with the present invention.

The detector 22 illustrated in FIG. 1, may be implemented by means of a bridge circuit. FIG. 2A shows Wheatstone strain bridge 30 with a constant voltage supply 32 being applied between supply terminals 34 and 36. The Wheatstone bridge 30 has four arms labeled A, B, C and D. Arm A of the bridge 30 may include a measuring gauge 38 similar to the strain gauge 20 fixed to the outer wall of the container 12 containing the expanding concrete mixture or sample 11. Arm B of the bridge 30 may be dummy strain gauge 40, i.e., a strain gauge in an environment similar to that of the measuring gauge in arm A. The dummy gauge 40 likewise may be cemented to a container of the type used herein, but filled with a non-expanding, temperature compensating mixture, for example, Plaster of Paris. The dummy gauge 40 monitors a thermal mass similar to the sample 11, thereby cancelling out the effects of changing temperatures upon measured samples.

Bridge arms C and D employ precision resistors 42 and 44 mounted in an instrument case. A potentiometer 46 is in series with resistor 44 in arm C. Strain gauge readings are indicated by means of a dial attached to potentiometer 46 as it nulls a sensitive null galvanometer 48, which is coupled across the null terminals 50 and 52 of the bridge 30.

The schematic drawing of FIG. 2A illustrates the basic elements of a detector circuit. However, other improvements might be provided. For example, the resistor 44 may include a bank or multiplicity of resistors (not shown) connected in turn by a radial switch. These resistors may be adjusted to represent increments of, for example, 100 strain units while the potentiometer 46 may represent individual strain units thereby increasing the range of the instrument while retaining adequate sensitivity. Likewise, the position of the potentiometer 46 in the bridge schematic is arbitrary because various strain gauge measuring instruments could place it in the other arms.

The bridge 30 may be P350A strain bridge manufactured by Vashay Instruments of Measurements Group, Inc. Such a device was used to collect the data referred to in FIGS. 3A–3D and FIG. 4. The bridge had a switch to increase the range of the instrument and a dummy gauge was used for all the measurements. A more advanced type of digital bridge, for example, a Vashay 3500 provides strain measurements equaling those of the P350A. The Vashay 3500 is somewhat easier to use. Both instruments may be utilized in the so-called quarter bridge mode. In such an arrangement, the bridge uses a standard resistor instead of the dummy strain gauge 40 in arm B. The dummy gauge is preferred when temperature excursions are anticipated. The quarter bridge mode is somewhat easier to implement. Another useful strain bridge is a Baldwin SR4 strain bridge which is excited by a constant voltage AC source.

Figure 2B:
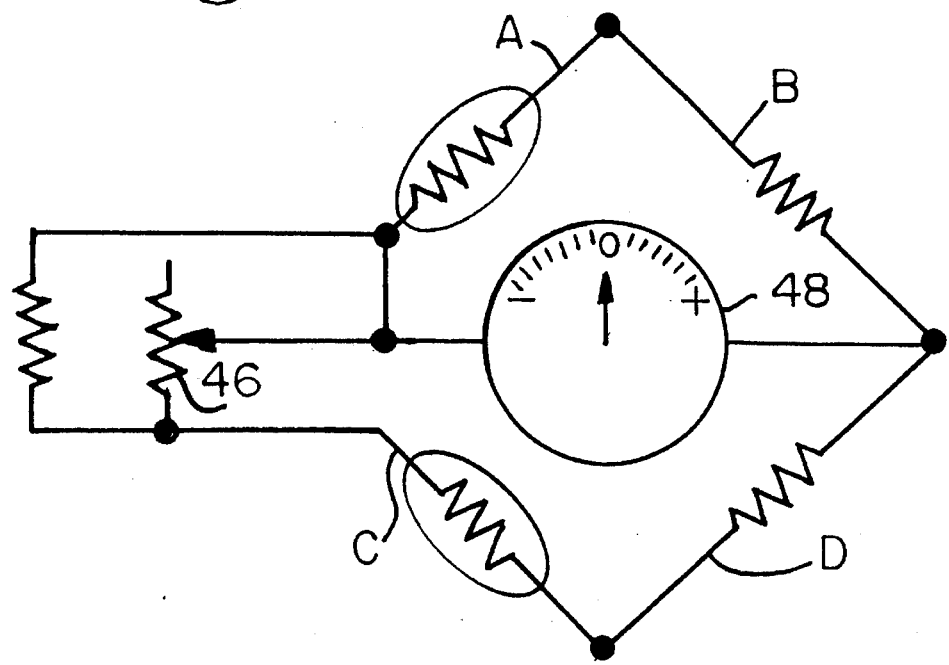
Figure 3A:
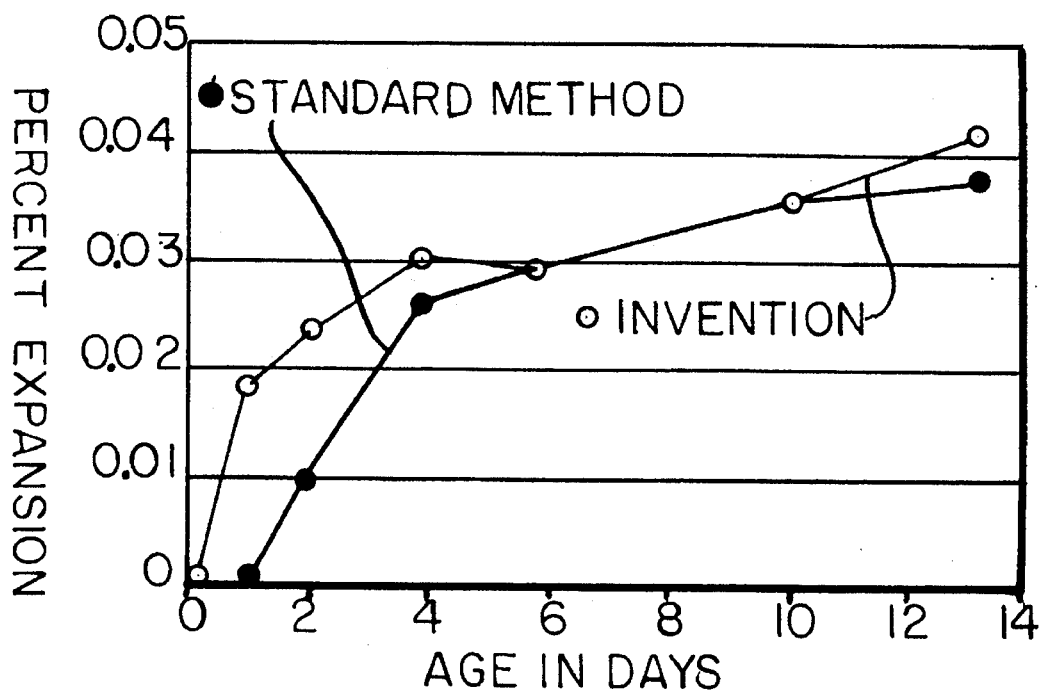
FIGS. 3A–3D are comparative plots of expansion over time of test samples performed according to a known method and the method of the invention.
Figure 3B:
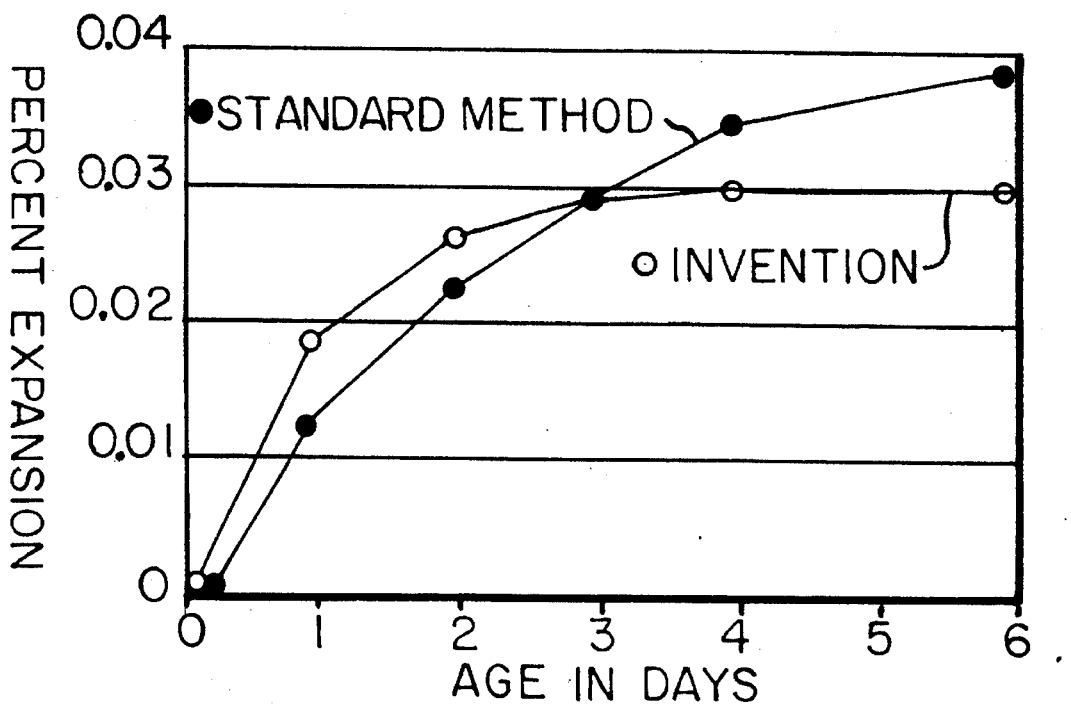
Figure 3C:
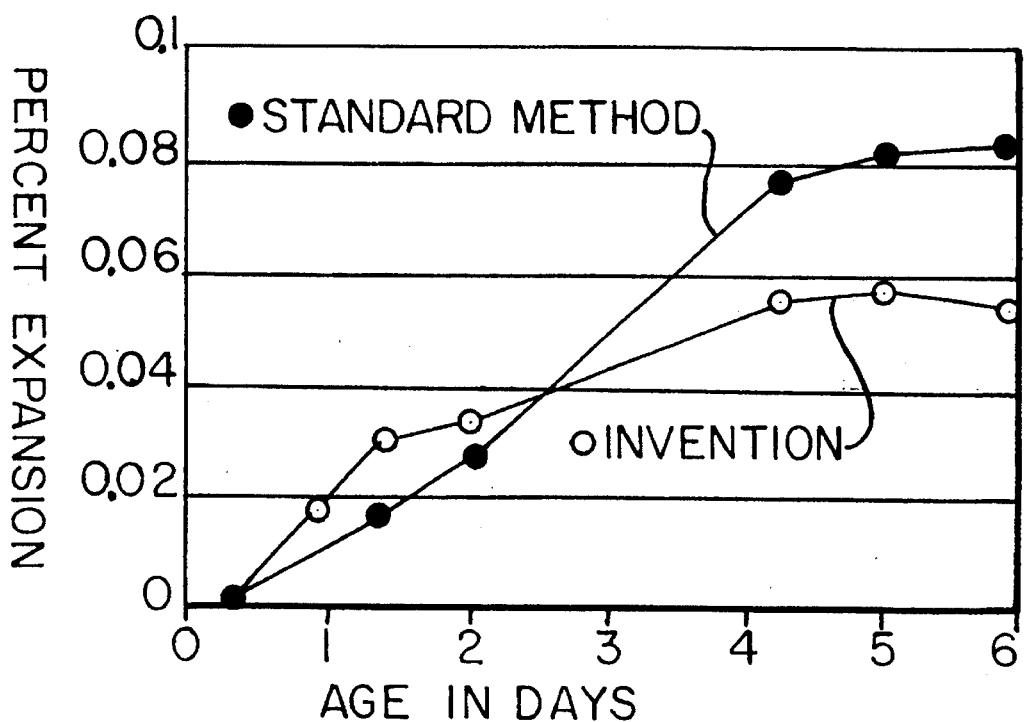
Figure 3D:
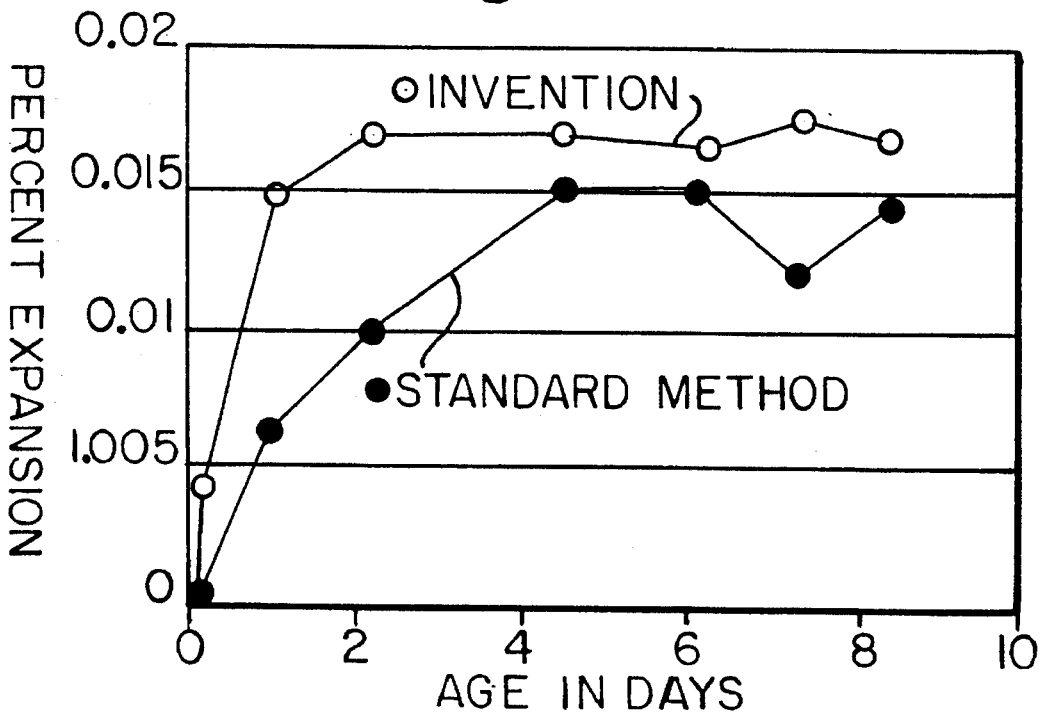

Another example of a useful strain measuring apparatus is illustrated in FIG. 2B. The device is based on the so called Cary-Foster bridge configuration. In the arrangement illustrated, the potentiometer 46 is coupled in the galvanometer circuit between arms A and C, and the dummy gauge is also in arm C.

Strain gauges of various types are well known. For example, strain gauges may be formed of grids of thin wire bonded to a paper substrate. When these devices are glued to a structural member, strains in the member are translated into a changing resistance in the gauge. Another type of gauge is a foil gauge prepared by sputtering a grid of vacuum deposited metal on a foil substrate. Other gauges employ a semiconductor material. In the present invention, a CEA-060-250-UN-350 foil gauge was used to take the measurements hereinafter discussed.

Referring again to FIG. 1, the container 12 has an overall height H and a diameter D. The sample 11 is poured into the container 12 to a sample height $H_s$. Curing fluid 32 is deposited or poured over the sample 11 to a height $H_c$. The sample 11 comprises various components including cement 33 and aggregate 34. According to the invention, the maximum aggregate size is not limited to one inch as in the described prior arrangements, because the interior of the container 12 is unobstructed. For example, in an exemplary embodiment, the container 12 has a diameter D which is about 6¾ inches and an overall height of about 8¼ inches. The sample height $H_s$ is about 7 inches and the curing fluid height $H_c$ is about 1 inch.

In accordance with the invention, the sample of concrete 11 is placed in the container 12 to within about one inch of the top 18. In practice, the concrete 11 is compacted in three layers, each of which is rodded 25 times using a standard concrete testing placement technique. Immediately after the concrete is compacted and finished, the curing water 32 is poured over the concrete 11 to a depth of about 1 inch. The filled pail is placed where it will not be disturbed, and where its surrounding temperature will remain approximately constant while measurements of concrete expansion are made.

The initial concrete sample 11 is relatively stiff and begins to harden in the container 12 soon after placement therein. Upon hardening, expansion of the sample 11 is transferred laterally to the container 12. This expansion is sensed by the strain gauge.

The present invention has a number of advantages over the previously described ASTM standard test. For example, the test may be performed by personnel with little training. Also, according to the invention, the sample 11 need not be demolded to make measurements. Indeed, data recording begins as soon as the material is properly placed in the container 12 and begins to harden. Thus, there is no delay before useful data may be acquired, and it is unlikely that data will be lost due to destruction of the sample.

Also, as previously noted, samples containing large maximum sizes of coarse aggregate may be tested. This is important because these materials minimize concrete drying shrinkage. In the prior method, placement of the restraining cage limits the maximum aggregate size to about one inch. In the present invention, the maximum aggregate size may be increased up to about ⅓ of the container diameter. In the arrangement illustrated, the maximum aggregate size is about 2".

Finally, the present invention allows the test to be conducted on the construction site without the need for transferring the samples to a laboratory. Thus, the job supervisor has physical possession and control of the samples. Also, current expansion information which may be utilized to tailor how the job is completed is on-site.

FIGS. 3A–3D are comparative plots illustrating test data obtained utilizing the standard method and the method according to the present invention. As can be readily appreciated, there is a correlation between the data obtained by both methods. Some of the data obtained in accordance with the standard method, however, appears to be erratic. This may be due to the difficulty associated with making standard measurements.

As illustrated in FIGS. 3A–3D, the initial expansions of the concrete filled container occur at a faster rate than those associated with the standard method. However, the faster rate may to some degree be caused by the plotting convention, because no compensation is made in the graphs for the delay of several hours in reading the standard samples. Generally, the maximum allowable expansion is limited to an amount, e.g., 0.15% where concrete deterioration occurs. In general, acceptable expansion occurs in a range of about 0.02% and about 0.1%. A particularly useful range of expansions is about 0.03% and 0.07%. The data from both tests generally intersect at an expansion of about 0.03% which is near the lower end of the range and is generally considered to be optimum for floor slabs. Consequently, the measurement results achieved by both methods appear to be about the same in the range of optimum expansion. When the expansions are greater than 0.03%, the standard method indicates expansions that are greater than those produced by the present invention. Conversely, for expansions less than 0.03%, the standard method is usually, but only slightly, greater than those indicated by the present invention.

Figure 4:
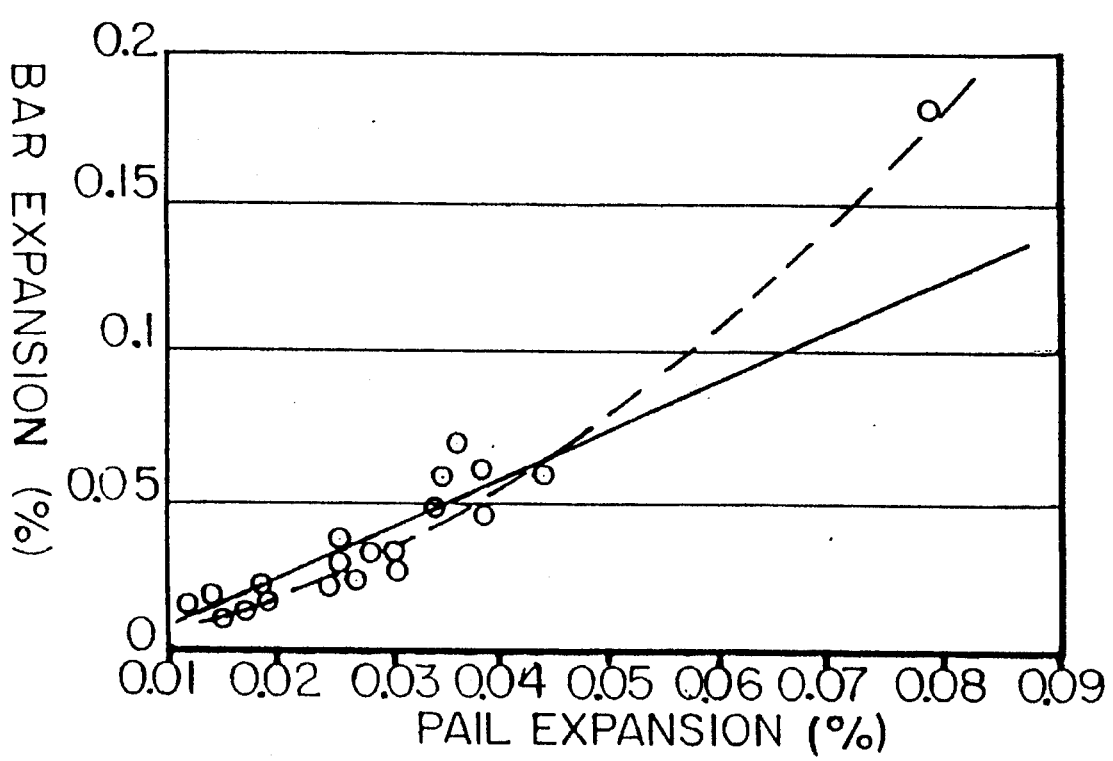
FIG. 4 is a plot of data collected by both methods illustrating the correlation of the methods.

FIG. 4 is a comparison of the standard method as a percent of expansion versus the expansion as a percent in accordance with the present invention. The data is a random compilation of data points taken from both methods. The data were taken either at the ultimate expansion or at a four day cutoff point. The clustering of the data indicates that the standard method and the method in accordance with the present invention correlate well in the optimum range. As can be appreciated from FIG. 4, there does not seem to be a straight line relationship between data points taken by the standard method and that of the present invention. The curved dashed line appears to provide a better fit for the data points. This suggests that a more complicated relationship between the test procedures may exist. However, as noted above, in the lower expansion ranges, the methods correlate well.

Differences between data obtained by the standard method and the present invention are probably affected by the fact that the container 12 has a greater stiffness than the single threaded rod of the standard method. Further, the container 12 confines the sample 11 more completely than the restraining cage of the standard test. For example, the bar in the restraining cage secures the concrete only along one axis, whereas the container 12 restrains the sample radially in 360°. Also, the sample 11 in the container 12 is farther from the source of curing water 32 which is deposited on the top of the sample. The concrete in the comparatively thin bar in the standard method is immersed completely in the curing water. The lack of curing water at the depth where the strain gauge is located appears to limit expansion more quickly, while the molded bars in the standard method continue to expand. The exposure to curing water on the top and the radial restriction of the sample in the container 12 are probably closer to conditions inside a typical concrete slab than the conditions which occur in the standard test. The data therefore indicates that the method can be used to closely approximate the standard test values, especially when concrete expansions are near the optimum of about 0.03%.

The simplicity of the present invention, the capacity of the container to accommodate concrete with large size coarse aggregate, the ease of recording strain gauge data and the availability of data at the test site provide great advantages over the prior method. Most importantly, however, is the elimination of much human error caused by the difficulty of implementing the prior arrangements.

In an exemplary embodiment, the container 12 is a 26 gauge steel cylindrical one gallon pail, (approximately 8¼"H×6 ¾"D) having a welded seam, manufactured by Central Can and available through Palmer Supplies Co., Cleveland, Ohio. Extruded cans, if available, may also be used. The strain gauge is a CEA-06-250uw-120. An SB-10 switch balance may be employed for connecting up to 10 pails to a P-3500 strain indicator with 326DFV wire, these components are manufactured by and available from Measurements Group, Inc. of Raleigh, N.C. The strain gauge may be secured to the container 12 by a cyanoacrylate adhesive sold under the name M-Bond 200 by Micro-Measurements and available from Measurements Group, Inc.

While there have been described what are at present considered to be the preferred embodiments of the present invention, it will be apparent to those skilled in the art that various changes and modifications may be made therein without departing from the invention, and it is intended in the appended claims to cover such changes and modifications as fall within the spirit and scope of the invention.

What is claimed is:

1. Apparatus for measuring volumetric changes in hardenable samples comprising:

a steel container having an open top and an uninterrupted upstanding sidewall for receiving and containing a hardenable sample therein in intimate and direct contact with an inner surface of said sidewall; and strain gauge means secured to the sidewall of the container and being disposed for sensing expansive changes in said sidewall in response to volumetric changes in the sample upon hardening and being operable when energized to produce a signal indicative of such volumetric changes in the sample.

2. The apparatus of claim 1 wherein the strain gauge means comprises a resistive element in which resistance changes with length.

3. The apparatus of claim 1 further including bridge circuit means coupled to resistor elements of the strain gauge means.

4. The apparatus of claim 1 further comprising metering means coupled to the strain gauge means for producing an output corresponding to the strain of the strain gauge means resulting from volumetric changes in the sample.

5. The apparatus of claim 1 further comprising means for recording the signal indicative of volumetric changes in the hardenable sample.

6. The apparatus of claim 5 wherein the means for recording comprises at least one of an electronic memory, data logger and a pen recorder.

7. The apparatus of claim 5, the strain gauge means comprising a plurality of strain gauges, and further comprising switch means coupled to the plurality of strain gauges and to the means for recording for selectively coupling data from multiple samples to said means for recording.

8. The apparatus of claim 1 wherein the cylinder is about 26 gauge steel.

9. The apparatus of claim 1 wherein the sample has a maximum coarse aggregate size of about ⅓ the diameter of the cylinder.

10. The apparatus of claim 1 wherein the sample has a maximum coarse aggregate size of at least 2".

11. The apparatus of claim 1 wherein the sample has an expansion in a range of 0.02% and 0.1%.

12. The apparatus of claim 1 wherein the sample has an expansion in a range of about 0.03% and 0.07%.

13. The apparatus of claim 1 further including a second container and strain gauge coupled in a bridge configuration with the means strain gauge means for recording a temperature compensating sample for comparison with the hardenable sample.

14. The apparatus of claim 1 wherein the sample is shrinkage compensated concrete.

15. The apparatus of claim 1, wherein the container has a closed bottom wall secured to the sidewall.

16. A method for measuring volumetric changes in curable samples comprising the steps of: disposing a sample of curable material into intimate and direct contact with an inner surface of a steel container having an open top and an uninterrupted upstanding cylindrical sidewall, securing a strain gauge to said sidewall to sense expansive changes of the sidewall in response to volumetric changes in the sample; and recording on-site volumetric changes in the sample in accordance with the changes in the strain gauge.

17. The method of claim 16, wherein the container has a closed bottom wall secured to the sidewall.

* * * * *